(12) United States Patent
Lilga et al.

(10) Patent No.: US 9,777,224 B2
(45) Date of Patent: Oct. 3, 2017

(54) METHODS FOR CONVERSION OF LIGNOCELLULOSIC-DERIVED PRODUCTS TO TRANSPORTATION FUEL PRECURSORS

(71) Applicant: BATTELLE MEMORIAL INSTITUTE, Richland, WA (US)

(72) Inventors: Michael A. Lilga, Richland, WA (US); Asanga B. Padmaperuma, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 15/345,305

(22) Filed: Nov. 7, 2016

(65) Prior Publication Data

US 2017/0130138 A1    May 11, 2017

Related U.S. Application Data

(60) Provisional application No. 62/253,007, filed on Nov. 9, 2015.

(51) Int. Cl.

| | |
|---|---|
| C10L 1/16 | (2006.01) |
| C07C 1/00 | (2006.01) |
| C07C 13/15 | (2006.01) |
| C10G 3/00 | (2006.01) |
| C07D 307/33 | (2006.01) |

(52) U.S. Cl.
CPC ............ *C10G 3/44* (2013.01); *C07D 307/33* (2013.01); *C10G 2400/04* (2013.01)

(58) Field of Classification Search
CPC ..... C07D 307/33; C10G 3/44; C10G 2400/04

USPC ............................ 549/326; 585/14, 240, 324
See application file for complete search history.

(56) References Cited

U.S. PATENT DOCUMENTS

| 8,362,306 B2 | 1/2013 | Wheeler et al. |
| 9,428,704 B2 | 8/2016 | Chheda et al. |
| 2013/0079566 A1 | 3/2013 | Lin |

FOREIGN PATENT DOCUMENTS

WO    2015144994 A1    10/2015

OTHER PUBLICATIONS

Lilga et al, New Catalytic Conversion of Lignocellulosic Biomass to Hydrocarbon Fuels, BETO 2015 Project Peer Review, Mar. 2015, p. 1-24.*
Pham et al, Ketonization of Carboxylic Acids: Mechanisms, Catalysts, Implications for Biomass Conversion, ACS Catalysis, 2013, 3, p. 2456-2473.*
Bond, J. Q., et al., Interconversion between γ-valerolactone and pentenoic acid combined with decarboxylation to form butene over silica/alumina, Journal of Catalysis, 281, 2011, 290-299.
Karimi, E., et al., Thermal Decomposition of Acetic and Formic Acid Catalyzed by Red Mud—Implications for the Potential Use of Red Mud as a Pyrolysis Bio-Oil Upgrading Catalyst, Energy Fuels, 2010, 24, 2747-2757.

(Continued)

*Primary Examiner* — T. Victor Oh
(74) *Attorney, Agent, or Firm* — James D. Matheson

(57) ABSTRACT

Methods are disclosed for converting a biomass-derived product containing levulinic acid and/or gamma-valerolactone to a transportation fuel precursor product containing diesel like hydrocarbons. These methods are expected to produce fuel products at a reduced cost relative to conventional approaches.

9 Claims, 4 Drawing Sheets

(56) References Cited

OTHER PUBLICATIONS

Karimi, E., et al., Ketonization and deoxygenation of alkanoic acids and conversion of levulinic acid to hydrocarbons using a Red Mud bauxite mining waste as a catalyst, Catalysis Today, 190, 2012, 73-88.
Schwartz, T. J., et al., Energy densification of levulinic acid by thermal deoxygenation, Green Chemistry, 2010, 12, 1353-1356.

* cited by examiner

METHODS FOR CONVERSION OF LIGNOCELLULOSIC-DERIVED PRODUCTS TO TRANSPORTATION FUEL PRECURSORS

CROSS REFERENCE TO RELATED APPLICATIONS

This is a non-provisional application that claims priority from U.S. Provisional Patent Application No. 62/253,007 filed 9 Nov. 2015, which is incorporated in its entirety herein.

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to conversion of carbohydrates to biorenewable hydrocarbon fuels. More particularly, the invention relates to methods for conversion of lignocellulosic-derived products including levulinic acid and gamma-valerolactone to hydrocarbon fuel precursors suitable for transportation fuels.

BACKGROUND OF THE INVENTION

Lignocellulosic biomass is biomass composed of cellulose, hemicellulose, and lignin derived from plant-based materials including wood from trees and forest residues; grasses, stovers (e.g., corn), bagasse (e.g., sugarcane), straw, some algaes (e.g., filamentous algae), and like materials. Lignocellulosic biomass has a wide variety of potential uses, for example, for production of renewable energy, bioethanol, transportation fuels, commodity chemicals, and other materials that could one day reduce demands on existing oil supplies, and could one day reduce demands on existing grain supplies used currently to produce ethanol. Presently, fermentation of grain sugars is a well-known process for producing ethanol used as a common blend stock in gasoline and for production of some commodity chemicals. However, finding a replacement for ethanol is not trivial. For example, while other hydrocarbons can be produced by fermentation, biochemical approaches leading to such hydrocarbons are not always compatible with complex biomass hydrolysate streams. Further, while some approaches have been investigated for converting lignocellulosic biomass feedstocks to transportation fuels, these approaches typically require extensive capital expenditures and high operation costs stemming from multistep procedures, complex chemistries, elevated processing conditions (e.g., high temperatures and high pressures), or energy-intensive operations. As a result, simple and cost-effective replacements are still being sought. In particular, a need still exists for processes that can provide paraffin- and isoparaffin-containing fuels such as diesel and aviation that also have an ability to reduce: capital requirements for processing equipment, processing steps, energy consumption, and operation costs that can also work in the existing commercial infrastructure and can use lignocellulosic materials as feedstocks. The present invention is an important step in addressing these needs.

SUMMARY OF THE INVENTION

The present invention includes a method for conversion of a lignocellulosic biomass-derived product to a transportation fuel precursor product by reacting a biomass-derived lignocellulosic bioproduct that includes levulinic acid and/or gamma-valerolactone (or combinations thereof) and a reducing agent over a catalyst at ambient pressure and a temperature from 340° C. to 450° C. to generate the transportation fuel precursor product that includes a diesel-like hydrocarbon mixture that has an organic oil phase with a boiling range similar to diesel fuel, and an aqueous phase product. (In some embodiments about 40 to 60% of the diesel-like hydrocarbon mixture boils in the range of about 25 to 300° C. and any remainder boils at a temperature above 240° C.)

In some embodiments the catalyst is a ketonization catalyst such as a cerium-zirconia catalyst (in one embodiment 17% cerium on a zirconia support), a lanthanum zirconia catalyst, or a cerium-lanthanum zirconia catalyst. While these types of catalysts are specifically described, other catalysts may also be utilized. The reducing agents utilized are typically chemicals such as ethylene glycol, formic acid, or xylitol, and in some instances these are produced from fermentation, hydrogenation, or decomposition of sugars. In addition the feedstock material including levulinic acid and/or gamma-valerolactone may also be derived from sugars.

In some embodiments the method further comprises the step of recycling the aqueous-phase product (which typically contains at least one of the group of alcohols, ketones and aldehydes) back into the feed to enrich the reactant stream and increase the yield of open chain olefins in the diesel-like hydrocarbon mixture. The lignocellulosic bioproduct may be introduced to the catalyst in an aqueous feed.

The present invention also includes a method for conversion of a lignocellulosic biomass-derived product to a transportation fuel precursor product. The method includes a single step of: reacting a biomass-derived lignocellulosic bioproduct that includes levulinic acid in an aqueous feed containing a reducing agent over a catalyst that includes cerium on a zirconia support at ambient pressure and a temperature from 340° C. to 450° C. to generate a diesel-like hydrocarbon mixture.

The present invention also includes a single-step method for forming gamma-valerolactone from a biomass-derived lignocellulosic product that includes levulinic acid. The method includes the single step of: reacting the biomass-derived lignocellulosic product including levulinic acid with a ketonization catalyst at ambient pressure at a temperature from 300° C. to 350° C. to generate the gamma-valerolactone product.

The purpose of the foregoing abstract is to enable the United States Patent and Trademark Office and the public generally, especially the scientists, engineers, and practitioners in the art who are not familiar with patent or legal terms or phraseology, to determine the nature and essence of the technical disclosure of the application. The abstract is neither intended to define the invention of the application, which is measured by the claims, nor is it intended to be limiting as to the scope of the invention in any way.

DETAILED DESCRIPTION

In one embodiment of the invention, a method is described for converting a lignocellulosic biomass-derived feedstock that includes levulinic acid (LA), gamma-valerolactone (GVL), or a mixture of the two to a transportation fuel precursor product containing a complex mixture of diesel-like hydrocarbons that is suitable for upgrading for generating transportation fuels. In the following description, embodiments of the present invention are shown and described by way of illustration of the best mode contemplated for carrying out the invention. It will be clear that the invention may include various modifications and alternative constructions. Accordingly, the description of the preferred embodiments should be seen as illustrative only and not limiting. The present invention includes all modifications, alternative constructions, and equivalents falling within the spirit and scope of the invention as defined in the claims.

Figure 1:
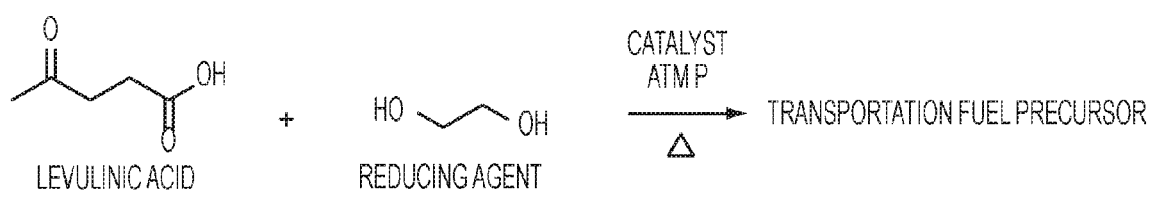
FIG. 1 shows an exemplary process for conversion of lignocellulosic derived bioproducts to a transportation fuel precursor product, according to one embodiment of the present invention.

FIGS. 1-4 show various aspects of several exemplary embodiments of the invention. Referring first to FIG. 1, an exemplary process for conversion of lignocellulosic derived bioproducts to a transportation fuel precursor is shown. As shown in the figure, a lignocellulosic bioproduct containing levulinic acid (LA) and or gamma-valerolactone (GVL) derived from biomass from any of a variety of organic products or waste streams, is introduced in an aqueous stream to a ketonization catalyst under specific temperatures, preferably (340° C.-450° C. more preferably 350° C.-400° C.), and low pressures (e.g., ambient) to generate a transportation fuel precursor product which includes a diesel-fuel-like hydrocarbon mixture including open-chain olefins and paraffins. The precursor product can be further upgraded, such as by hydrogenation, hydrodeoxygenation, and/or distillation, to generate various types of transportation fuels. In addition to the diesel-like precursor product, an aqueous phase product is also produced that includes soluble hydrocarbons such as alcohols, aldehydes, and ketones. This product may be separated for other uses or processing, or can be recycled back into the process as an enriching agent to increase the yield of open-chain olefins in the subsequent fuel precursor products. The transportation fuel precursor product produced by this method is surprising. Prior examples and methodologies would suggest that ketonization of LA with basic catalysts would produce ring-closed products such as cyclopentenones (T. J. Schwartz, A. R. P. van Heiningen and M. C. Wheeler, Green Chem., 2010, 12, 1353-1356), or that heating GVL (formed by hydrogenation of LA) over a solid acid $SiO_2/Al_2O_3$ catalyst results in loss of $CO_2$ with formation of butenes, rather than a complex hydrocarbon mixture like the transportation fuel precursor produced in the present method. (J. Q. Bond, D. Wang, D. M. Alonso, J. A. Dumesic, Journal of Catalysis 281 (2011) 290-299).

In the preferred embodiment, the aqueous feed stream contains a reducing agent, preferably an organic reducing agent, such as ethylene glycol (EG), formic acid (FA), isopropanol (IPA), or polyols such as xylitol. These reducing agents hydrogenate and dehydrate the LA during processing that enhance the formation of open-chain hydrocarbons rather than allowing formation of closed-ring compounds as would be expected when LA is reacted with a ketonization catalyst under conventional conditions. The present embodiment uses ketonization catalysts such as cerium zirconia catalysts ($Ce/ZrO_2$), or lanthanum zirconia catalysts ($La/ZrO_2$) that combine weak acid and weak base functionalities. The catalyst hydrogenates LA to GVL with the organic reducing agent. Preferably, this reaction takes place at a temperature from about 300° C. to about 350° C. When higher temperatures are used, for example, from about 340° C. to about 400° C., the reaction with the organic reducing agent and LA and/or GVL tends to drive loss of $CO_2$ and oligomerization which results in the formation of the transportation fuel precursor product. Experiments run to date show that at concentrations of GVL in water of up to about 22 wt %, nearly complete conversion of GVL is observed at temperatures from about 360° C. to about 400° C. Concentrations of GVL above 34 wt % give nearly complete conversion at a temperature of 380° C. Conversion above 50% occurs at temperatures from about 340° C. to about 360° C.

Figure 2:
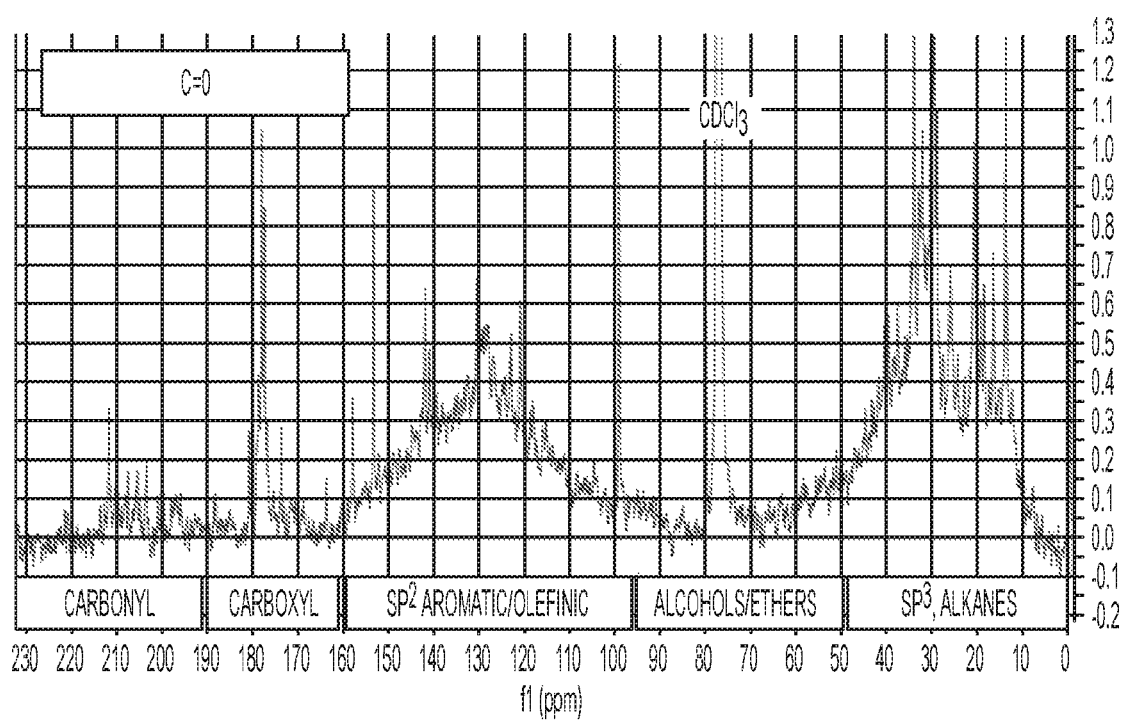
FIG. 2 is a $^{13}$C NMR spectrum showing a typical distribution of hydrocarbons found in transportation precursor products produced by the present invention.

The higher-temperature product is made up of a variety of diesel-like hydrocarbons including high-boiling open-chain olefins, and saturated paraffin hydrocarbons. FIG. 2 is a $^{13}$C NMR spectrum showing the distribution of hydrocarbons found in an exemplary transportation fuel precursor product formed by the process of the present invention from the reaction of LA and FA. TABLE 1 lists functional group contents estimated by integration of the $^{13}$C NMR spectrum.

TABLE 1

| FUNCTIONAL GROUP | CONTENT* |
| --- | --- |
| Carbonyls (ketones, aldehydes) | 3% |
| Carbonyls (acids, lactones) | 5% |
| $sp^2$ carbons (olefins, aromatics) | 40% |
| $sp^3$ carbons (saturated alkanes) | 52% |

*Determined by $^{13}$C NMR

Figure 3:
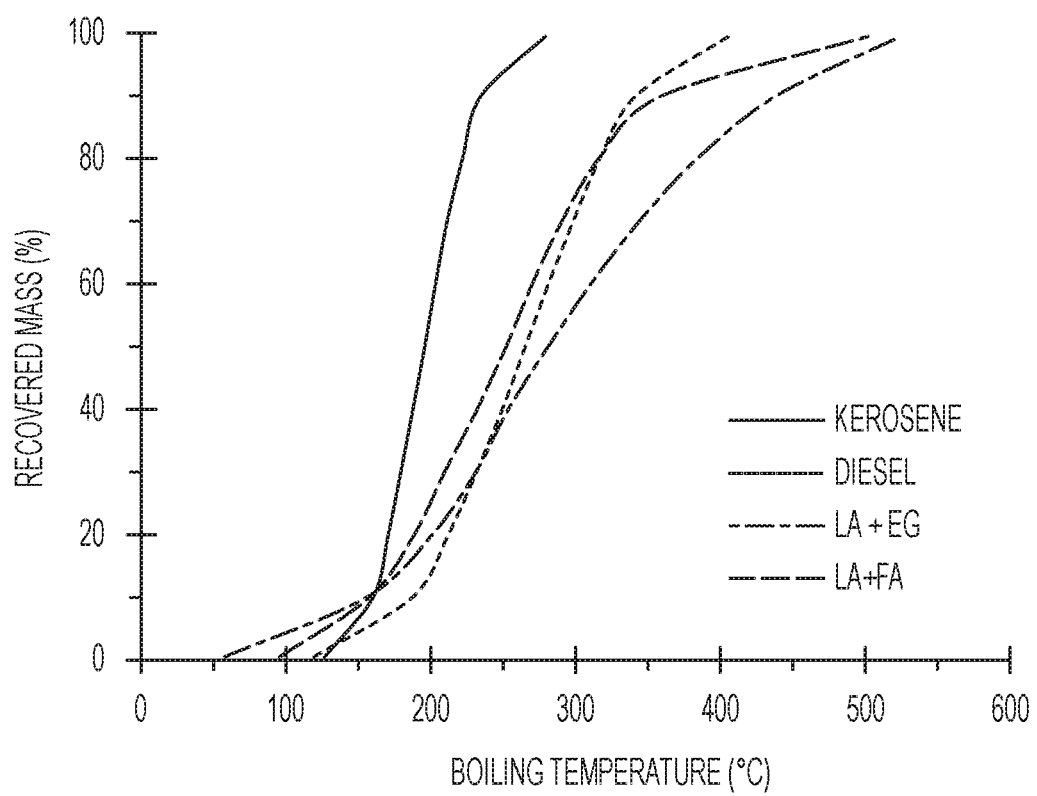
FIG. 3 is a plot that compares distillation curves of two exemplary precursor products produced by the present invention from exemplary feeds to kerosene and diesel fuels.
Figure 4:
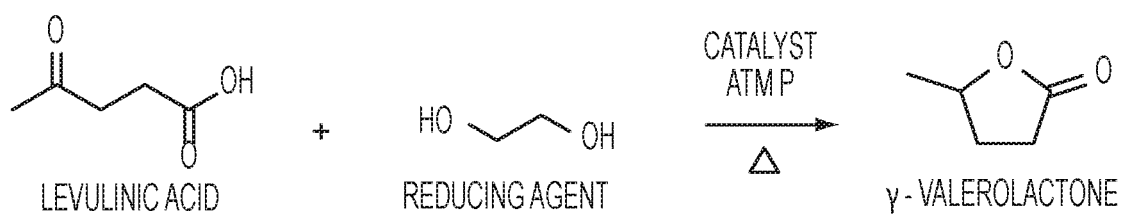
FIG. 4 shows an exemplary process for conversion of lignocellulosic derived bioproducts to gamma-valerolactone, according to another embodiment of the present invention.

Data in the table reflect a heavy preference for olefins and saturated alkanes typical of transportation fuels. FIG. 3 is a plot showing exemplary results from the simulated distillation of two products obtained from selected feeds (LA+EG; and LA+FA) from the described process when compared to kerosene and diesel fuels. Like typical fuel products, transportation fuel precursor products resulting from the present process include hydrocarbons, which typically distill in a temperature range from about 25° C. to about 390° C. These fuel-range hydrocarbons can be upgraded and fractionated under typical processes to produce gasoline, jet, diesel, other aviation fuels, and fuel blend stocks suitable for commercial and military applications, and for heating fuels. Examples of specific embodiments of the present invention and testing thereof are described hereafter.

Example 1

1 g of a $Ce/ZrO_2$ ketonization catalyst (e.g., a 60-100 mesh MEL XZO 802 17% $CeO_2$ on zirconium hydroxide catalyst, MEL Chemicals, Manchester, UK) was loaded in a reactor tube (3/8" OD) and heated to 330° C. with a flow of $N_2$ gas (10 mL/min) at atmospheric pressure. An aqueous feed consisting of 4.19 g LA (0.036 moles), 2.29 g EG (0.036 moles), and 58.86 g water (10 wt % total organic) was then fed to the reactor at a flow rate of 0.05 mL/min. Samples were collected over a 4.5 hr period. Temperature was then increased to 380° C. and samples were collected for an additional 4 hr. At the lower temperature, testing demonstrated that GVL was produced, as illustrated by the exemplary process presented in FIG. 4. At the higher temperature, a complex mixture of high-boiling diesel-like hydrocarbons was produced including a majority of open-chain olefins and unsaturated paraffins. In addition, an aqueous phase product was also recovered that included soluble hydrocarbons with carbon numbers at or below C3 including, for example, acetaldehyde, ethanol, and acetone. No GVL was found in the aqueous product. Feeds containing up to 50% LA and EG [1:1] yield the same organic products.

Example 2

2.2 g of $Ce/ZrO_2$ catalyst was loaded in a reactor tube (e.g., 3/8" OD) and heated to 400° C. with a flow of $N_2$ gas (10 mL/min) at atmospheric pressure. An aqueous feed consisting of 2.83 g LA (0.024 moles), 1.17 g FA (0.025 moles), and 41.36 g water (8.8 wt % total organic) was then introduced into the reactor at a flow rate of 0.05 mL/min. Samples were collected over a 6 hr period. Products included an organic phase product with a complex mixture of high-boiling diesel-like hydrocarbons containing open-chain olefins, and an aqueous phase product comprising soluble hydrocarbons and ketones. When equimolar concentrations of LA and FA were used in the aqueous feed, complete conversion of LA was obtained, and an organic phase product similar to that obtained with EG resulted. Whether the reducing agents are added to the process, are inherent in the feed by virtue of another prior process, bio-reaction or other activity, results obtained in this process are the same.

Example 3

5.0 g of $Ce/ZrO_2$ catalyst (60-100 mesh) was loaded in a reactor tube (e.g., 1/2" OD) and heated to 380° C. with a flow of $N_2$ gas (10 mL/min) at atmospheric pressure. An aqueous feed consisting of 3.62 g GVL (0.0362 moles), 1.71 g FA (0.0371 moles), and 21.2 g water (20 wt % total organic) was then introduced into the reactor at a flow rate of 0.05 mL/min. Samples were collected over a 4 hr period. The temperature of the reactor was increased to 400° C. and samples were collected over another 3 hr period. The liquid feed was stopped, the gas feed was changed to air, and the reactor was heated to 450° C. for 4 hr to conduct an in-situ coke burn.

The air feed was stopped, the $N_2$ gas feed was restarted, and the temperature set to 360° C. An aqueous feed consisting of 6.05 g GVL (0.0604 moles), 2.90 g FA (0.0630 moles), and 18.4 g water (33 wt % total organic) was then introduced into the reactor at a flow rate of 0.03 mL/min. Samples were collected over a 4 hr period. The temperature of the reactor was set to 380° C. and samples were collected over another 3 hr period. The temperature of the reactor was set to 400° C. and samples were collected over another 3 hr period. The liquid feed was stopped, the gas feed was changed to air, and the reactor was heated to 450° C. for 4 hr to conduct an in-situ coke burn.

The air feed was stopped, the $N_2$ gas feed was restarted, and the temperature set to 340° C. An aqueous feed consisting of 12.00 g GVL (0.1199 moles), 5.50 g FA (0.1195 moles), and 17.50 g water (50 wt % total organic) was then introduced into the reactor at a flow rate of 0.03 mL/min. Samples were collected over a 4 hr period. The temperature of the reactor was set to 360° C. and samples were collected over another 3 hr period. The temperature of the reactor was set to 380° C. and samples were collected over another 3 hr period.

Products in all cases included an organic phase product with a complex mixture of high-boiling diesel-like hydrocarbons containing open-chain olefins, and an aqueous phase product comprising soluble hydrocarbons and ketones. Complete conversion of GVL was obtained for the 20 and 33 wt % feeds. For the 50 wt % feed, GVL conversions of 66, 79, and 99% were obtained at 340° C., 360° C., 380° C., respectively. $^{13}$C NMR analyses estimated the functional group compositions to be those shown in Table 2. The results show that catalyst activity is easily restored with an in-situ coke burn.

TABLE 2

| Temp, °C. | Functional Group Content, %* | | | | | |
|---|---|---|---|---|---|---|
| | Aromatic | Olefin | Carbonyl | Carboxyl | Ether/Alcohol | Alkane |
| 400 | 19.6 | 8.5 | 3.5 | 0.4 | 1.3 | 66.7 |
| 380 | 10.6 | 14.2 | 4.1 | 0.5 | 1.4 | 69.2 |
| 360 | 7.2 | 15.3 | 5.0 | 1.7 | 0.8 | 70.0 |
| 340 | 7.8 | 9.1 | 3.1 | 4.1 | 1.4 | 74.4 |

*Determined by $^{13}$C NMR

The present invention addresses previously unmet needs in the art for conversion of lignocellulosic biomass products. The invention provides a reaction pathway to fuel precursor products that 1) contain primarily normal paraffins and isoparaffins suitable as feedstocks for production of, for example, diesel and aviation fuels, in a simple, less expensive method than is required by the prior art. While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the scope of the present invention.

What is claimed is:

1. A method for conversion of a lignocellulosic biomass reactant to a transportation fuel product, comprising the single step of:
reacting a lignocellulosic biomass reactant comprising levulinic acid and/or gamma-valerolactone and a reducing agent in an aqueous feed over a lanthanum-zirconia ketonization catalyst at ambient pressure and a temperature from 340° C. to 450° C. to generate a diesel hydrocarbon mixture product and an aqueous phase product.

2. The method of claim 1 wherein the reducing agent is selected from the group consisting of ethylene glycol, formic acid, and xylitol.

3. The method of claim 1, further comprising the step of recycling the aqueous-phase product back into the feed to enrich the reactant stream and increase the yield of open-chain olefins in the diesel hydrocarbon mixture product.

4. The method of claim 1, wherein about 40 to 60% of the diesel hydrocarbon mixture product boils in the range from about 25° C. to about 300° C.

5. The method of claim 1, wherein the aqueous phase product comprises at least one of the group consisting of alcohols, ketones, and aldehydes.

6. A method for conversion of a lignocellulosic biomass reactant to a transportation fuel product, comprising the single step of:

reacting a lignocellulosic biomass reactant comprising levulinic acid and/or gamma-valerolactone in an aqueous feed containing a reducing agent over a cerium-lanthanum-zirconia ketonization catalyst at ambient pressure and a temperature from 340° C. to 450° C. to generate a diesel hydrocarbon mixture product and an aqueous phase product.

7. The method of claim 6, wherein the reducing agent is selected from the group consisting of ethylene glycol, formic acid, and xylitol.

8. The method of claim 6, further comprising the step of recycling the aqueous-phase product comprising alcohols, ketones, and aldehydes back into the feed to enrich the reactant stream and increase the yield of open chain olefins in the diesel hydrocarbon mixture product.

9. A single-step method for forming gamma-valerolactone from a lignocellulosic biomass reactant comprising levulinic acid, the method comprising the single step of: reacting the lignocellulosic biomass reactant in an aqueous feed comprising levulinic acid in the presence of an organic reducing agent over a lanthanum-zirconia ketonization catalyst at ambient pressure at a temperature from 300° C. to 350° C. to generate gamma-valerolactone.

* * * * *